(12) United States Patent
Schrier et al.

(10) Patent No.: US 8,435,799 B2
(45) Date of Patent: May 7, 2013

(54) EVALUATING HEPARIN PREPARATIONS FOR PHARMACEUTICAL USE

(75) Inventors: David Schrier, Somerville, MA (US); Nur Sibel Gunay, Brookline, MA (US); Megan Sucato, Quincy, MA (US); Stephen Smith, Milford, MA (US); Zachary Shriver, Cambridge, MA (US)

(73) Assignee: Momenta Pharmaceuticals, Inc., Cambridge, MA (US)

( * ) Notice: Subject to any disclaimer, the term of this patent is extended or adjusted under 35 U.S.C. 154(b) by 528 days.

(21) Appl. No.: 12/203,574

(22) Filed: Sep. 3, 2008

(65) Prior Publication Data

US 2010/0050748 A1 Mar. 4, 2010

(51) Int. Cl.
*G01N 30/02* (2006.01)

(52) U.S. Cl. .......................................... 436/161; 514/56

(58) Field of Classification Search ........................ None
See application file for complete search history.

(56) References Cited

U.S. PATENT DOCUMENTS

2004/0198697 A1 10/2004 Cohen et al.

OTHER PUBLICATIONS

Kishimoto, Takashi Kei, et al. Contaminated Heparin Associated with Adverse Clinical Events and activation of the Contact System, Apr. 23, 2008, The New England Journal of Medicine, vol. 358(23), pp. 2457-2467.*
Turnbull, J.E., Analytical and preparative strong anion-exchange HPLC of heparan sulfate and heparin saccharides, 2001, Methods in Molecular Biology, vol. 171, pp. 141-147.*
Guerrini, M. et al., "Oversulfated Chondroitin sulfate is a contaminant in heparin associated with adverse clinical events", Nature Biotechnology Jun. 2008 Nature Publishing Group US, vol. 26, No. 6, pp. 669-675 (2008).
Bartolucci, C et al., "Inhibition of human leukocyte elastase by chemically and naturally oversulfated galactosaminoglycans" Carbohydrate Research, vol. 276, No. 2, pp. 401-408 (1995).
Rice, KG et al., "Gradient Page and Strong Anion Exchange Sax Hplc as Analytical Tools for Sequencing the Heparin Polymer", American Chemical Society. Abstracts of Paper. At the National Meeting, vol. 193, p. 1, (1987).
Trehy, M L et al., "Analysis of heparin sodium by SAX/HPLC for contaminants and impurities" Journal of Pharmaceutical and Biomedical Analysis, vol. 49, No. 3, pp. 671-673 (2009).
International Search Report and Written Opinion from International Application Serial No. PCT/US2009/055792 mailed Feb. 12, 2009.

* cited by examiner

*Primary Examiner* — Robert Xu
(74) *Attorney, Agent, or Firm* — Lando & Anastasi LLP

(57) ABSTRACT

The disclosure features methods of analyzing preparations of heparin, and materials derived from heparin using strong anion exchange high performance liquid chromatography (SAX-HPLC).

21 Claims, 1 Drawing Sheet

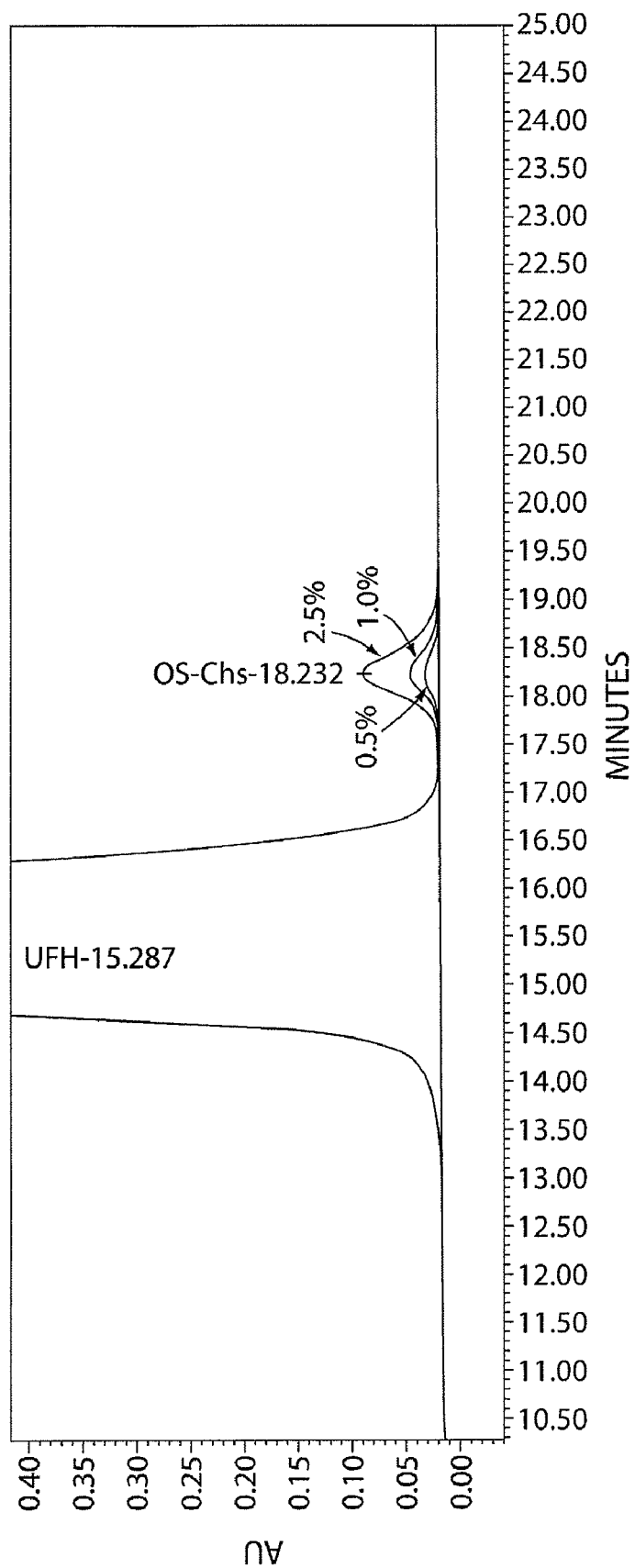

EVALUATING HEPARIN PREPARATIONS FOR PHARMACEUTICAL USE

The invention relates to methods of analyzing samples heparin, and materials derived from heparin.

BACKGROUND

Complex polysaccharides have been used as pharmaceutical interventions in a number of disease processes, including oncology, inflammatory diseases, and thrombosis. Examples of pharmaceutical interventions in this class are hyaluronic acid, an aid to wound healing and anti-cancer agent, and heparin, a potent anticoagulant and anti-thrombotic agent. Complex polysaccharides elicit their function primarily through binding soluble protein signaling molecules, including growth factors, cytokines and morphogens present at the cell surface and within the extracellular matrices between cells, as well as their cognate receptors present within this environment. In so doing, these complex polysaccharides effect critical changes in extracellular and intracellular signaling pathways important to cell and tissue function. For example, heparin binds to the coagulation inhibitor anti-thrombin III promoting its ability to inhibit factor Ia and Xa.

SUMMARY

In one aspect, the disclosure features a method of evaluating a heparin preparation that includes: providing a heparin preparation; analyzing the heparin preparation by SAX-HPLC to determine the absence or presence of over sulfated chondrotin sulfate (OSCS), wherein the limit of detection of the OSCS in the heparin preparation is 0.05% (w/w), the OSCS is resolved from baseline and the OSCS is resolved from other components of the heparin preparation. The evaluation can be, e.g., to determine suitability for use as a pharmaceutical or for use in making a pharmaceutical. The method can include making a decision, e.g., to classify, select, accept or discard, release or withhold, process into a drug product, ship, move to a different location, formulate, label, package, release into commerce, sell or offer for sale the preparation, based, at least in part, upon the analysis.

In an embodiment, OSCS is not present or is present below the limit of detection and the preparation is suitable to be used as a pharmaceutical product or for the preparation of a pharmaceutical product. In an embodiment, the method can include providing a record, e.g., certificate of analysis regarding OSCS content, or other print or computer readable record, for a preparation determined to be suitable for use as a pharmaceutical or for use in making a pharmaceutical. The record can include other information, such as a specific test agent identifier, a date, an operator of the method, or information about the source, structure. In an embodiment, the method further includes making decision to select, accept, release, process into a drug product, ship, move to a different location, formulate, label, package, release into commerce, or sell or offer for sale the preparation.

In an embodiment, the OSCS is present at or above the limit of detection and the preparation is not suitable to be used as a pharmaceutical product or for the preparation of a pharmaceutical product. In an embodiment, the method can include providing a record, e.g., certificate of analysis regarding OSCS content, or other print or computer readable record, for a preparation determined not to be suitable for use as a pharmaceutical or for use in making a pharmaceutical. The record can include other information, such as a specific test agent identifier, a date, an operator of the method, or information about the source, structure. In an embodiment, the method further includes making a decision to discard or withhold the preparation.

In an embodiment the method further includes memorializing the decision or step taken.

In an embodiment, the preparation is selected from the group of a starting material for the production of a drug, an intermediate in the production of a drug, a drug substance or a drug product. In an embodiment, the heparin preparation is an unfractionated heparin preparation.

In an embodiment, the method further includes providing a heparin preparation which does not include OSCS or includes OSCS below the limit of detection and evaluating the ability of the preparation to induce an immune response or react with an anti-OSCS antibody.

In an embodiment, the method further includes providing a heparin preparation which includes OSCS at or above the limit of detection and evaluating the ability of the preparation to induce an immune response or react with an anti-OSCS antibody.

In an embodiment, the method further includes calibrating a SAX-HPLC column with a standard that includes between 0.05% (w/w) and 1.0% (w/w) OSCS, e.g., 0.05% (w/w), 0.1% (w/w), 0.5% (w/w), 1.0% (w/w) OSCS.

In an embodiment, the heparin preparation is analyzed using a SAX-HPLC column that has been calibrated with a standard that includes between 0.05% (w/w) and 1.0% (w/w) OSCS, e.g., 0.05% (w/w), 0.1% (w/w), 0.5% (w/w), 1.0% (w/w) OSCS.

In an embodiment, run time for the SAX-HPLC is not more than 1 hour, 45 minutes, 30 minutes, 20 minutes or 15 minutes. In an embodiment, the run time for the SAX-HPLC is between about 15 to 45 minutes, 20 to 40 minutes or 30 to 35 minutes.

In one aspect, the disclosure features a method of evaluating a heparin preparation that includes: receiving information on OSCS content, wherein the information was obtained by a method described herein, making a decision, e.g., to classify, select, accept or discard, release or withhold, process into a drug product, ship, move to a different location, formulate, label, package, release into commerce, sell or offer for sale the preparation, based, at least in part, upon receipt of the information.

In one aspect, the disclosure features a method of evaluating a heparin preparation that includes: obtaining information regarding OSCS content, wherein the information was obtained by a method described herein, and transmitting the information to a party which makes a decision, e.g., to classify, select, accept or discard, release or withhold, process into a drug product, ship, move to a different location, formulate, label, package, release into commerce, sell or offer for sale the preparation, based, at least in part, upon the information.

In another aspect, the disclosure features a method of detecting OSCS in a heparin preparation. The method includes providing a heparin preparation and analyzing the heparin preparation by a SAX-HPLC method that has a limit of detection of 0.05% (w/w), resolves OSCS from a baseline and resolves OSCS from other components of the heparin preparation, to thereby detect OSCS in the heparin preparation.

In an embodiment, when OSCS is detected, the method further includes making a decision, e.g., a decision described herein. For example, when OSCS is detected in the heparin preparation, the method further includes making a record, classifying, discarding, withholding, purifying the heparin preparation based, at least in part, upon the analysis or when OSCS is not detected in the heparin preparation, the method further includes making a record, classifying, selecting, accepting, processing into a drug product, ship, moving to a different location, formulating, labeling, packaging, releasing into commerce, selling or offering for sale the heparin preparation, based, at least in part, upon the analysis.

In an embodiment, the preparation is selected from the group of a starting material for the production of a drug, an intermediate in the production of a drug, a drug substance or a drug product. In an embodiment, the heparin preparation is an unfractionated heparin preparation.

In an embodiment, the method further includes calibrating a SAX-HPLC column with a standard that includes between 0.05% (w/w) and 1.0% (w/w) OSCS, e.g., 0.05% (w/w), 0.1% (w/w), 0.5% (w/w), 1.0% (w/w) OSCS.

In an embodiment, the heparin preparation is analyzed using a SAX-HPLC column that has been calibrated with a standard that includes between 0.05% (w/w) and 1.0% (w/w) OSCS, e.g., 0.05% (w/w), 0.1% (w/w), 0.5% (w/w), 1.0% (w/w) OSCS.

In an embodiment, run time for the SAX-HPLC is not more than 1 hour, 45 minutes, 30 minutes, 20 minutes or 15 minutes. In an embodiment, the run time for the SAX-HPLC is between about 15 to 45 minutes, 20 to 40 minutes or 30 to 35 minutes.

In one aspect, the disclosure features a method of determining the amount of OSCS in a heparin preparation. The method includes providing a heparin preparation and analyzing the heparin preparation by a SAX-HPLC method that that has a limit of detection of 0.05% (w/w), resolves OSCS from a baseline and resolves OSCS from other components of the heparin preparation, to thereby determine the amount of OSCS in the heparin preparation.

In an embodiment, the method includes providing a record, e.g., certificate of analysis regarding OSCS content, or other print or computer readable record, for a preparation determined to be suitable for use as a pharmaceutical or for use in making a pharmaceutical. The record can include other information, such as a specific test agent identifier, a date, an operator of the method, or information about the source, structure or amount of OSCS.

In an embodiment, when OSCS is detected, the method further includes making a decision, e.g., a decision described herein.

In an embodiment, the preparation is selected from the group of a starting material for the production of a drug, an intermediate in the production of a drug, a drug substance or a drug product. In an embodiment, the heparin preparation is an unfractionated heparin preparation.

In an embodiment, the method further includes calibrating a SAX-HPLC column with a standard that includes between 0.05% (w/w) and 1.0% (w/w) OSCS, e.g., 0.05% (w/w), 0.1% (w/w), 0.5% (w/w), 1.0% (w/w) OSCS.

In an embodiment, the heparin preparation is analyzed using a SAX-HPLC column that has been calibrated with a standard that includes between 0.05% (w/w) and 1.0% (w/w) OSCS, e.g., 0.05% (w/w), 0.1% (w/w), 0.5% (w/w), 1.0% (w/w) OSCS.

In an embodiment, run time for the SAX-HPLC is not more than 1 hour, 45 minutes, 30 minutes, 20 minutes or 15 minutes. In an embodiment, the run time for the SAX-HPLC is between about 15 to 45 minutes, 20 to 40 minutes or 30 to 35 minutes.

In one aspect, the disclosure features a standard preparation or a set of standard preparations. The standard includes a solvent and OSCS of between about 0.05% (w/w) and 1.0% (w/w) OSCS, e.g., 0.05% (w/w), 0.1% (w/w), 0.5% (w/w), 1.0% (w/w) OSCS. The set includes a plurality of standards each having a different concentration of OSCS. In one embodiment, the solvent can be an unfractionated heparin preparation that does not contain a detectable amount of OSCS. The standard or set of standards can be used to calibrate a SAX-HPLC column. The column can be used in the methods described herein.

In another aspect, the invention features making a preparation, e.g., a standard preparation of known concentration, by providing OSCS of between about 0.05% (w/w) and 1.0% (w/w) OSCS, e.g., 0.05% (w/w), 0.1% (w/w), 0.5% (w/w), 1.0% (w/w) OSCS, and combining it with a solvent, e.g., a solvent described herein.

A heparin preparation, as used herein, is a preparation which contains heparin or a preparation derived therefrom, and thus includes UFH, LMWH, ULMWH and the like.

The term "unfractionated heparin (UFH)" as used herein, is heparin purified from porcine intestinal mucosa that can be used as a drug or as starting material in the process to form a LMWH.

Complex polysaccharide drug products can be isolated or derived from natural sources and are complex mixtures of polysaccharide chains. It is important that UFH, whether used as a drug or as a starting material for the preparation of a heparin-derived drug, e.g., a LMWH, not contain unacceptable levels of OSCS. The methods described herein are useful, e.g., from a process standpoint, e.g., to monitor or ensure batch to batch consistency or quality and to identify heparin preparations that may or may not result in an adverse patient reaction. An adverse patient reaction might be local irritation, pain, edema, peripheral edema; local reactions at the injection site (e.g., skin necrosis, nodules, inflammation, oozing), systemic allergic reactions (e.g., pruritus, urticaria, anaphylactoid reactions), coma or death.

Over sulfated chondrotin sulfate (OSCS), as used herein, refers to chondrotin sulfate having the following structure

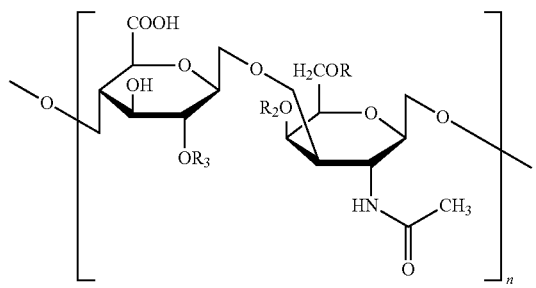

wherein $R_1$ is $SO_3H$, $R_2$ is $SO_3H$ and $R_3$ is either H or $SO_3H$.

The term "limit of detection" refers to the minimum concentration of OSCS that can be distinguished from other components in a heparin preparation.

The limit of detection can be used as a reference value. A reference value can be a value for the presence of OSCS in a sample, e.g., a reference sample. The reference value can be numerical or non-numerical. E.g., it can be a qualitative value, e.g., yes or no, or present or not present at a preselected level of detection, or graphic or pictorial. The reference value can also be a release standard (a release standard is a standard which should be met to allow commercial sale of a product) or production standard, e.g., a standard which is imposed, e.g., by a party, e.g., the FDA, on a heparin preparation.

The SAX-HPLC methods described herein resolve OSCS from a baseline level. The baseline is a value or starting point from which a reaction can be measured. When OSCS is present in a heparin preparation at or above the limit of detection, the methods described herein can distinguish OSCS from the baseline on a chromatogram.

The methods described herein also allow for OSCS to be resolved from other components of the heparin preparation. The terms "resolve", "resolved", "resolving" mean to render two things as distinct. For example, the methods described herein distinguish OSCS from other components of the heparin preparation. In addition, the methods described herein distinguish the presence of OSCS at levels as low as 0.05% (w/w) from the baseline.

The details of one or more embodiments of the invention are set forth in the accompanying drawings and the description below. Other features, objects, and advantages of the invention will be apparent from the description and drawings, and from the claims.

DETAILED DESCRIPTION

The drawing is briefly described.

FIG. 1 is a chromatograph of unfractionated heparin (UFH) spiked with various concentrations of over sulfated chondroitin sulfate (OSCS), namely 0.5% (w/w) OSCS, 1.0% (w/w) OSCS and 2.5% (w/w) OSCS.

SAX-HPLC

Preferably about 100 µl to 300 µl of sample is loaded onto the column. Substrates, e.g., resins or beads, suitable for SAX-HPLC include those with strong anionic groups such as quaternary ammonium groups. The substrate can be of various particle sizes, including 10 µm, 15 µm, 20 µm, 30 µm. The particles can be spherical. In an embodiment, the substrate is SOURCE™ 15Q or RESOURCE™ 15Q from Amersham Biosciences.

Useful mobile phases include a salt such as tris hydrochloride, sodium chloride, and combinations thereof. In some embodiments, the mobile phase uses a gradient of a salt. The gradient can be either a linear or non-linear gradient. For example, the gradient can be multiphasic, e.g., biphasic, triphasic, etc. The flow rate is preferably about 1.0 to 1.4 ml/minute. The mobile phase can be maintained at a constant or near-constant pH, e.g., a pH of about 7.0, 7.5, 8.0 or 8.5.

The column can be maintained at a constant temperature throughout the separation, e.g., using a commercial column heater. In some embodiments, the column can be maintained at a temperature from about 10° C. to about 30° C., e.g., about 10° C., 15° C., 18° C., 20° C., 22° C., 25° C., 30° C.

OSCS separated from a heparin preparation by the methods described herein can be detected by numerous means including, e.g., by ultraviolet absorbance (e.g., at a wavelength of about 215 nm).

Additionally, a standard can be used in the methods described herein. Examples of standards include OSCS at a predetermined concentration and/or an unfractionated heparin preparation that does not have a detectable level of OSCS. The OSCS standard can be in a solvent. In an embodiment, the OSCS standard can be in a preparation of heparin that does not have a detectable level of OSCS.

EXAMPLE

SAX-HPLC was used to detect OSCS present at various concentrations in a preparation of unfractionated heparin. OSCS was added to five samples of the unfractionated heparin preparation at the following concentrations, 5.0% (w/w), 2.5% (w/w), 1.0% (w/w), 0.5% (w/w) and 0.1% (w/w). In addition, the unfractionated heparin sample and an OSCS standard (1% (w/w)) were used as controls. Mobile phase A (10 mM Tris Hydrochloride, pH 7.5) was combined with each of the samples in polypropylene HPLC vials. Mobile phase B was 10 mm Tris Hydrochloride, 2M sodium chloride at pH 7.5.

The gradient conditions were as follows:

| HPLC Gradient Conditions: Time, minutes | % Mobile Phase A | % Mobile Phase B |
|---|---|---|
| 0.0 | 97 | 3 |
| 2.5 | 97 | 3 |
| 7.5 | 90 | 10 |
| 22.5 | 0 | 100 |
| 25.0 | 0 | 100 |
| 25.1 | 97 | 3 |
| 30.0 | 97 | 3 |

The samples were held at 25° C. during analysis and 100 µl of sample was injected onto the column. The samples were separated using a Triton SOURCE™ Q15 4.6×100 mm strong anion column (Amersham Biosciences) at 25° C. at a flow rate of 1.0 ml/min over 30 min of total run time. Ultraviolet absorbance was detected at 215 nm. The results are shown in FIG. 1.

The references, patents and patent applications cited herein are incorporated by reference. Modifications and variations of these methods and products thereof will be obvious to those skilled in the art from the foregoing detailed description and are intended to be encompassed within the scope of the appended claims.

What is claimed is:

1. A method of evaluating a heparin preparation, comprising:
   providing a heparin preparation to determine its suitability for use as a drug or in the preparation of a drug, wherein the heparin preparation is suitable for use as a drug or in the preparation of a drug when OSCS is not present or is present below the limit of detection; and
   analyzing the heparin preparation by SAX-HPLC to determine the absence or presence of over sulfated chondrotin sulfate (OSCS), wherein the limit of detection of OSCS in the heparin preparation is 0.05% (w/w), the OSCS is resolved from a baseline and the OSCS is resolved from other components of the heparin preparation, to thereby evaluate the heparin preparation.

2. The method of claim 1, further comprising making a decision about the heparin preparation based upon the analysis.

3. The method of claim 2, wherein OSCS is present at or above the limit of detection and the decision is classifying, discarding, or withholding the preparation.

4. The method of claim 2, wherein OSCS is not present at the limit of detection and the decision is classifying, selecting, accepting, releasing, processing into a drug product, shipping, moving to a different location, formulating, labeling, packaging, releasing into commerce, selling or offering for sale the preparation.

5. The method of claim 1, wherein the heparin preparation is an unfractionated heparin preparation.

6. The method of claim 1, further comprising calibrating a SAX-HPLC column with a standard that includes between 0.05% (w/w) and 1.0% (w/w) OSCS.

7. The method of claim 1, wherein the SAX-HPLC method uses a SAX-HPLC column that has been calibrated with a standard that includes between 0.05% (w/w) and 1.0% (w/w) OSCS.

8. The method of claim 1, wherein run time for the SAX-HPLC is not more than 45 minutes.

9. The method of claim 8, wherein the run time for the SAX-HPLC is not more than 30 minutes.

10. The method of claim 8, wherein the run time for the SAX-HPLC is between about 20 to 40 minutes.

11. A method of evaluating a heparin preparation comprising:
receiving information about OSCS content of a heparin preparation, wherein the information was obtained by a method that comprises providing the heparin preparation; and analyzing the heparin preparation by SAX-HPLC to determine the absence or presence of over sulfated chondroitin sulfate (OSCS), wherein the limit of detection of OSCS in the heparin preparation is 0.05% (w/w), wherein the heparin preparation is suitable for use as a drug or in the preparation of a drug when OSCS is not present or is present below the limit of detection, the OSCS is resolved from a baseline and the OSCS is resolved from other components of the heparin preparation; and
making a decision based upon the analysis, to thereby evaluate the heparin preparation.

12. The method of claim 11, wherein OSCS is present at or above the limit of detection in the heparin preparation and the decision is classifying, discarding, or withholding the preparation.

13. The method of claim 11, wherein OSCS is not present at the limit of detection and the decision is classifying, selecting, accepting, releasing, processing into a drug product, shipping, moving to a different location, formulating, labeling, packaging, releasing into commerce, selling or offering for sale the preparation.

14. The method of claim 11, wherein the heparin preparation is an unfractionated heparin preparation.

15. A method of evaluating a heparin preparation comprising:
determining information about OSCS content of a heparin preparation, wherein the information was obtained by a method that comprises providing the heparin preparation; and analyzing the heparin preparation by SAX-HPLC to determine the absence or presence of over sulfated chondrotin sulfate (OSCS), wherein the limit of detection of OSCS in the heparin preparation is 0.05% (w/w), wherein the heparin preparation is suitable for use as a drug or in the preparation of a drug when OSCS is not present or is present below the limit of detection, the OSCS is resolved from a baseline and the OSCS is resolved from other components of the heparin preparation; and
providing the information to a party which makes a decision about the heparin preparation based upon the analysis, to thereby evaluate the heparin preparation.

16. A method of detecting over sulfated chondrotin sulfate (OSCS) in a heparin preparation, comprising:
providing a heparin preparation;
analyzing the heparin preparation by a strong anion exchange high performance liquid chromatography (SAX-HPLC) method that has a limit of detection of OSCS in the heparin preparation of 0.05% (w/w), wherein the heparin preparation is suitable for use as a drug or in the preparation of a drug when OSCS is not present or is present below the limit of detection, the OSCS is resolved from a baseline and the OSCS is resolved from other components of the heparin preparation, to thereby detect OSCS in the heparin preparation, to thereby detect OSCS.

17. The method of claim 16, wherein OSCS is detected at or above the limit of detection in the heparin preparation and the method further comprises making a decision about the heparin preparation based upon the analysis.

18. The method of claim 16, wherein OSCS is not detected at the limit of detection in the heparin preparation and the method further comprises making a decision about the heparin preparation based upon the analysis.

19. A method of determining the amount of over sulfated chondrotin sulfate (OSCS) in a heparin preparation, comprising:
providing a heparin preparation;
analyzing the heparin preparation by a strong anion exchange high performance liquid chromatography (SAX-HPLC) method that has a limit of detection of OSCS in the heparin preparation of 0.05% (w/w), wherein the heparin preparation is suitable for use as a drug or in the preparation of a drug when OSCS is not present or is present below the limit of detection, the OSCS is resolved from a baseline and the OSCS is resolved from other components of the heparin preparation, to thereby determine the amount of OSCS in the heparin preparation.

20. The method of claim 19, wherein the method further comprises making a decision based upon the amount of OSCS present in the heparin preparation.

21. The method of claim 19, wherein the method further comprises making a decision about the heparin preparation based upon the amount of OSCS present in the heparin preparation.

* * * * *